(12) United States Patent
Kamrat

(10) Patent No.: US 9,632,025 B2
(45) Date of Patent: Apr. 25, 2017

(54) METHOD AND MEASURING DEVICE FOR CONTINUOUSLY MEASURING THE ABBE NUMBER

(71) Applicant: JANESKO OY, Vantaa (FI)

(72) Inventor: Esko Kamrat, Vantaa (FI)

(73) Assignee: JANESKO OY, Vantaa (FI)

( * ) Notice: Subject to any disclaimer, the term of this patent is extended or adjusted under 35 U.S.C. 154(b) by 55 days.

(21) Appl. No.: 14/702,364

(22) Filed: May 1, 2015

(65) Prior Publication Data
US 2015/0330896 A1 Nov. 19, 2015

(30) Foreign Application Priority Data

May 13, 2014 (FI) ...................................... 20145433

(51) Int. Cl.
*G01N 21/41* (2006.01)
*G01N 21/43* (2006.01)
*G01N 21/552* (2014.01)

(52) U.S. Cl.
CPC ............ *G01N 21/431* (2013.01); *G01N 21/41* (2013.01); *G01N 21/552* (2013.01); *G01N 2021/434* (2013.01); *G01N 2201/12* (2013.01)

(58) Field of Classification Search
CPC ...... G02B 15/177; G02B 13/18; G02B 13/22; G02B 13/04; G02B 15/14; G02B 17/08;
(Continued)

(56) References Cited

U.S. PATENT DOCUMENTS 4,682,889 A * 7/1987 Harmer ............... G01N 21/4133
356/135
4,699,511 A 10/1987 Seaver
(Continued)

FOREIGN PATENT DOCUMENTS

EP 0 359 167 A2 3/1990
FR 2 536 537 A1 5/1984

OTHER PUBLICATIONS

Dec. 1, 2014 Search Report issued in Finnish Application No. 20145433.

*Primary Examiner* — Michael P Stafira
(74) *Attorney, Agent, or Firm* — Oliff PLC

(57) ABSTRACT

Method and device for measuring the Abbe number in a process liquid. Light generates successively at wavelengths of 486.1 nm, 589.3 nm and 656.3 nm and different light wavelengths are directed successively through a measuring window in the process liquid so total reflection occurs at each wavelength on the measuring window surface and process liquid. Partial light reflected at each wavelength is directed to a sensor, whereby an image forms on the sensor surface; between light and dark boundary region corresponding to each wavelength critical angle, in which total reflection occurs. At each wavelength between light and dark boundary region detection by image analysis. At each wavelength, dependency between light and dark boundary region and refractive-index of process liquid measurement is detected, the Abbe number by refractive-index values obtained from:

Figure 1:
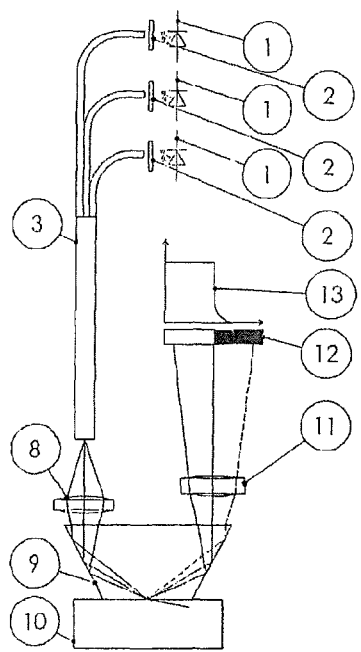

$$V_D = \frac{n_D - 1}{n_F - n_C};$$

$n_D$=refractive-index of process liquid to measure at 589.3 nm; $n_F$=refractive-index at 486.1 nm; and $n_C$=refractive-index at 656.3 nm.

20 Claims, 1 Drawing Sheet

(58) Field of Classification Search
CPC .............. G02B 27/0025; G02B 15/173; G02B 13/0045; G02B 15/20; G02B 17/0856; G02B 27/0172; G02B 17/0852
See application file for complete search history.

(56) References Cited

U.S. PATENT DOCUMENTS

| | | | | |
|---|---|---|---|---|
| 4,844,608 A | * | 7/1989 | Smith | G01N 21/43 356/136 |
| 5,502,560 A | * | 3/1996 | Anderson | G01N 21/431 356/128 |
| 5,617,201 A | * | 4/1997 | Kåhre | G01N 21/43 356/135 |
| 5,870,185 A | * | 2/1999 | See | G01N 21/4133 356/128 |
| 6,067,151 A | * | 5/2000 | Salo | G01N 21/4133 356/128 |
| 6,396,576 B1 | * | 5/2002 | Bleyle | G01N 21/43 356/128 |
| 6,876,444 B2 | | 4/2005 | Yilmaz et al. | |
| 2003/0169417 A1 | * | 9/2003 | Atkinson | G01N 21/4133 356/135 |
| 2007/0052949 A1 | * | 3/2007 | Salo | G01N 21/41 356/128 |
| 2007/0195312 A1 | | 8/2007 | Yilmaz et al. | |
| 2010/0141928 A1 | * | 6/2010 | Embry | G01N 21/4133 356/5.01 |
| 2012/0243002 A1 | * | 9/2012 | Yu | G01N 21/45 356/517 |
| 2013/0214138 A1 | * | 8/2013 | Chiarello | G01N 21/431 250/227.11 |
| 2014/0104601 A1 | * | 4/2014 | Baba | G01N 21/4133 356/135 |
| 2014/0268115 A1 | * | 9/2014 | Voipio | G01N 21/4133 356/128 |
| 2016/0116719 A1 | * | 4/2016 | Thompson | G02B 27/0062 359/356 |

* cited by examiner

METHOD AND MEASURING DEVICE FOR CONTINUOUSLY MEASURING THE ABBE NUMBER

The invention relates to a method and a measuring device for continuously measuring the Abbe number in a process liquid.

The background of the invention and the Abbe number are generally described below.

The Abbe number represents the magnitude of chromatic dispersion of a material. It describes the extent to which the material's refractive index varies according to the wavelength of light. Small Abbe numbers represent high dispersion and big Abbe numbers represent low dispersion, respectively. The Abbe number is defined as $$V_D = \frac{n_D - 1}{n_F - n_C},$$

where $n_D$ is the refractive index of the material at a wavelength of 589.3 nm, which is a standard wavelength in refractive index measurement. The refractive index $n_F$ is measured at a wavelength of 486.1 nm and $n_C$ at a wavelength of 656.3 nm.

In physics, different refractive indices mean that light propagates at different speeds in different materials. In normal dispersion, shortwave light propagates in a material slower than longwave light. Materials with a high refractive index usually have a small Abbe number, i.e. high dispersion. The Abbe number is used for classifying glass materials, for instance, but it may also be utilized in measuring process liquids.

It has long been possible to measure the Abbe number in laboratories with an Abbe refractometer, which has replaceable filters for the necessary wavelengths. A known solution is, for example, the device DR-M2 manufactured by a firm called Atago Co. Ltd. However, such solutions included in laboratory equipment cannot be directly applied to be used in continuous process measurement.

U.S. Pat. No. 6,876,444 B2 discloses a measurement principle without replaceable filters. In the solution described in U.S. Pat. No. 6,876,444 B2, a light source emitting white light is used and light from a measuring prism is split up by a diffraction grid or prism onto a light-sensitive cell of a two-dimensional CCD camera. The solution described in the publication allows the measurement of the refractive index at different wavelengths also by using wavelengths used in calculating the Abbe number. However, the solution described in the publication requires an optical part, with which white light is split up into different wavelengths. This makes the structure of the measuring device complex, as a two-dimensional camera cell must be used. Even though the device according to the invention described in the publication can measure dispersion properties of a sample at several wavelengths of light, the Abbe number is often sufficient to describe the dispersion properties of the sample. Literature values for dispersion of different substances are expressed as standard Abbe numbers in a table format.

The solution according to U.S. Pat. No. 6,876,444 B2 cannot be applied to continuous measurement of a process liquid.

The object of the invention is to provide a method and a measuring device that allow the prior art disadvantages to be eliminated. This is achieved by a method and measuring device of the invention. The method of the invention is characterized by generating light successively at wavelengths of substantially 486.1 nm, 589.3 nm and 656.3 nm and directing the lights of different wavelengths successively through the measuring window in contact with the process liquid to the process liquid, directing the part of light totally reflected at each wavelength to the sensor, detecting the boundary between the light and the dark region at each wavelength by means of an image analysis, determining at each wavelength the dependency between the boundary of the light and the dark region and the refractive index of the process liquid to be measured, and calculating the Abbe number by means of the refractive index values obtained from the aforementioned three wavelengths by using the formula known per se:

$$V_D = \frac{n_D - 1}{n_F - n_C}$$

where $n_D$ is the refractive index of the process liquid to be measured at a wavelength of 589.3 nm, $n_F$ is the refractive index at a wavelength of 486.1 nm, and $n_C$ is the refractive index at a wavelength of 656.3 nm.

The measuring device of the invention, for its part, is characterized in that the means for generating light comprise means for successively generating lights at wavelengths of substantially 486.1 nm, 589.3 nm and 656.3 nm, that the first directing means are arranged to direct the lights of different wavelengths successively through the measuring window in contact with the process liquid to the process liquid, that the second directing means are arranged to direct the part of light totally reflected at each wavelength successively to the sensor, that the arrangement for detecting the boundary between the light and the dark region and for determining the dependency between the boundary of the light and the dark region and the process liquid to be measured is arranged to perform the detection and determination at each wavelength, and that the measuring device further comprises a calculating unit for calculating the Abbe number by means of the refractive index values obtained from the aforementioned three wavelengths by using the formula known per se:

$$V_D = \frac{n_D - 1}{n_F - n_C}$$

where $n_D$ is the refractive index of the process liquid to be measured at a wavelength of 589.3 nm, $n_F$ is the refractive index at a wavelength of 486.1 nm, and $n_C$ is the refractive index at a wavelength of 656.3 nm.

The invention has, above all, the advantage that it provides a practical method and measuring device for continuously measuring the Abbe number in a process liquor. This has not been possible in the prior art.

Figure 2:
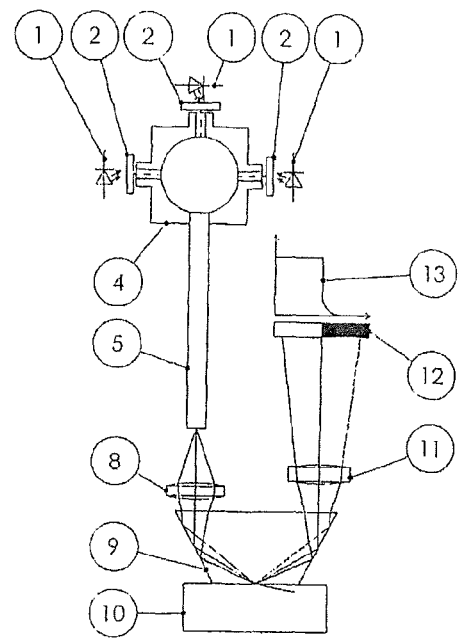
Figure 3:
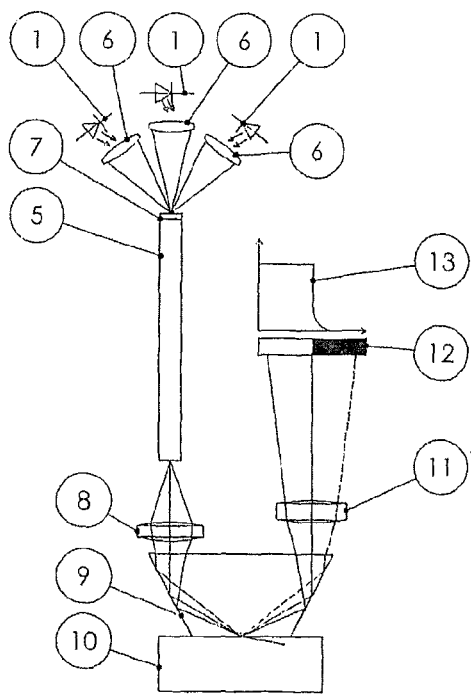
Figure 4:
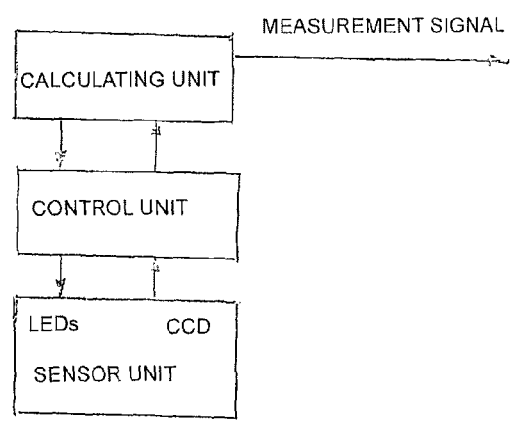

The invention will be described in the following by means of the attached drawing, in which FIG. 1 is a general view of a first embodiment of the measuring device of the invention, FIG. 2 is a general view of a second embodiment of the measuring device of the invention, FIG. 3 is a general view of a third embodiment of the measuring device of the invention, and FIG. 4 is a general view of the system of the measuring device of the invention.

FIGS. 1, 2 and 3 show the basic principle of the invention by means of three different embodiments. The invention utilizes a principle based on total reflection of light at the interface between a measuring window and a process liquid to be measured. This basic principle is known per se to a person skilled in the art and has been used for a very long time in process refractometers, for example. Said basic principle known per se is not described in greater detail herein. In this context, reference is made generally to publications in the field, such as U.S. Pat. No. 6,067,151, which describes said basic principle in more detail.

As FIGS. 1 to 3 show, three light sources 1 are used in the embodiments according to the figures. The light sources 1 are lit in successive order so that light is derived from one light source at a time. The light sources may be any suitable light sources, such as LEDs, the wavelengths of which are selected in such a manner that they correspond to standard wavelengths of 486.1 nm, 589.3 nm and 656.3 nm used for measuring the Abbe number. Alternatively, the light sources may be LEDs emitting white light or lamps emitting white light, in which case a filter 2 is provided in front of them. In such an embodiment, the filters 2 are selected such that they allow the wavelengths needed for measuring the Abbe number to pass through them.

FIG. 1 is a general view of a first embodiment, in which light from the different light sources 1 is combined into one and the same fiber 3. A fiber bundle may be used in the combination, whereby a certain number of fibers are arranged for each light source.

Light from the different light sources 1 may be combined by using an integrating sphere 4, for instance, as is shown in the embodiment according to FIG. 2. In the integrating sphere 4, the light is reflected in a diffuse way multiple times until illumination is distributed equally on the surface of the sphere. The integrating sphere 4 provides that the light from a plurality of light sources 1 has a uniform intensity. To lead the light forward from the integrating sphere, a fiber 5 may be used. The fiber may consist of a plurality of fibers with smaller diameters and forming a bundle. The fiber may also be an image fibre arranged to transmit an image.

FIG. 3 shows a third alternative embodiment of the invention. In this embodiment, light from the light sources 1 is combined into the same fiber 5 by using optics 6 and a light-diffusing member 7. The optics 6 may be implemented as either lens optics or by utilizing mirror optics. The diffusing member 7 may be ground glass, for instance.

From the fiber 3, 5, the light is directed by optics 8 to a prism 9 acting as a measuring window. The purpose of the optics 6 is to provide a suitable angular distribution for the light so that at a specific angle of light, total reflection occurs at the interface between the prism 9 and a process liquid 10. The optics 8 may be implemented with either lenses or mirrors or a combination thereof.

As can be seen in the figures, lights of different wavelengths arriving from the light sources 1 are arranged to be directed to the measuring window 9 by using first directing means comprising an optical fiber or optical fibers 3, 5 and lenses or mirrors or combinations thereof to provide a suitable angular distribution for the light arriving at the interface between the measuring window and the liquid to be measured.

At the interface between two substances, light is refracted in accordance with Snell's law:

$$n \sin \beta = n_i \sin \alpha, \quad (1)$$

where n is the refractive index of the substance to be measured, $\beta$ is the angle of light refracted at the interface in the substance to be measured with respect to the normal of the surface, $n_i$ is the refractive index of the measuring window, and $\alpha$ is the incidence angle of light at the interface of the substances with respect to the normal of the surface.

When the critical angle of total reflection is $$\sin \beta = \sin 90° = 1, \quad (2)$$

Snell's law has the form $$n = n_i \sin \alpha_c. \quad (3)$$

In equation (3), $\alpha_c$ is the critical angle of incidence, and larger inclination angles result in total reflection. In these equations, both the refractive index of the substance to be measured and the refractive index of the measuring window depend on the wavelength of light, and thus the critical angle $\alpha_c$ also depends on the wavelength.

In all embodiments according to FIGS. 1 to 3, the part of light that has been totally reflected is directed by an optical arrangement 11 to a light-sensitive sensor 12, such as a CCD camera. The CCD camera may be a line camera, for example. The light-sensitive surface is arranged in such a manner that the distance from the optical arrangement 11 equals exactly the focal length of the optical system 11. In this context, the optical arrangement 11 should be understood broadly to comprise an optical arrangement consisting of both lenses and mirrors or combinations thereof. It is advantageous to use mirror optics in the optics 8 and the optical arrangements 11 because, regardless of the wavelength of light, the mirror optics function in the same way. When implemented with lenses, the optics 8 and the optical arrangement 11 are lens systems in which chromatic aberration has been corrected.

An image 13 is formed on the light-sensitive surface of the sensor 12. The image has a boundary between the light and the dark region, which corresponds to the critical angle at which the total reflection occurs. Any conventional means for image analysis may be used for sensing the boundary between the light and the dark region.

By using known refractive index solutions, a connection between the boundary of the light and the dark region and the refractive index can be detected. This is determined for each light source separately. The refractive index of an unknown process liquid may thus be detected for each wavelength of light needed for determining the Abbe number. The Abbe number is determined by using the formula known per se:

$$V_D = \frac{n_D - 1}{n_F - n_C}$$

as was described above.

FIG. 4 shows system parts necessary for implementing the measuring device of the invention. The calculation of the refraction indices, the Abbe numbers derived therefrom and other variables is performed in a calculating unit. The calculating unit obtains the images of the camera (CCD) from a control unit. The control unit lights the LEDs one at a time in a desired order. A control signal is supplied to the control unit from the calculating unit. The calculating unit transmits the desired measurement signals, such as mA messages, to a control system of a production plant, for example.

Measurement of refraction indices and process liquid temperature may be used for determining the concentration of the process liquid, if components constituting the process liquid are known. The Abbe number may be used as additional information in determining the concentration or as an independent measure. The Abbe number and measurement performed at a standard wavelength may be utilized in continuous determination of process liquid composition ratios for different sorts of sugars, for instance. The Abbe number may also be used for determining organic and inorganic solution components and for detecting the average molecule size among macromolecular process substances. The invention allows the refractometer measurement to be also applied to areas where it has so far been necessary to combine multiple measurement techniques.

The invention is described above by means of embodiments shown in the figures. However, the invention is in no way restricted to the embodiments of the figures but may be freely modified within the scope of the accompanying claims.

The invention claimed is:

1. A method for continuously measuring the Abbe number in a process liquid, the method comprising the steps of:
generating light and directing the light through a measuring window in contact with the process liquid to the process liquid such that total reflection occurs on the surface of the measuring window and the process liquid, directing the part of the light that has been totally reflected to a sensor, whereby an image is formed on a light-sensitive surface of the sensor, the boundary between a light region and a dark region in the image corresponding to a critical angle at which the total reflection occurs, and detecting the dependency between the boundary of the light and the dark regions and the refractive index of the process liquid to be measured,
wherein the light is generated successively at wavelengths of substantially 486.1 nm, 589.3 nm and 656.3 nm and the light of different wavelengths is directed successively to the measuring window by means of optics to provide a suitable angular distribution for the light and directed through the measuring window in contact with the process liquid to the process liquid, and the part of the light totally reflected at each wavelength is directed to the sensor,
wherein the boundary between the light and the dark regions is detected at each wavelength by means of an image analysis, the dependency between the boundary of the light and the dark regions and the refractive index of the process liquid to be measured is determined at each wavelength, and the Abbe number is calculated by means of the refractive index values obtained from the aforementioned three wavelengths by using the formula known per se:

$$V_D = \frac{n_D - 1}{n_F - n_C}$$

where $n_D$ is the refractive index of the process liquid to be measured at a wavelength of 589.3 nm, $n_F$ is the refractive index at a wavelength of 486.1 nm, and $n_C$ is the refractive index at a wavelength of 656.3 nm.

2. A method as claimed in claim 1, wherein the light at the wavelengths of substantially 486.1 nm, 589.3 nm and 656.3 nm is generated by means of three different light sources.

3. A method as claimed in claim 2, wherein light sources emitting light at the aforementioned wavelengths are used as the light sources.

4. A method as claimed in claim 2, wherein light sources emitting white light are used as the light sources and a filter arranged in connection with each light source is used to provide a desired wavelength.

5. A method as claimed in claim 1, wherein the dependency between the boundary of the light and the dark regions and the refractive index of the process liquid to be measured is determined at each wavelength by utilizing information obtained from solutions with a known refractive index.

6. A method as claimed in claim 1, wherein the light that has been totally reflected is directed to the light-sensitive surface of the sensor by means of an optical arrangement.

7. A method as claimed in claim 1, wherein the light-sensitive surface is arranged with respect to the optical arrangement at a distance that equals the focal length of the optical arrangement.

8. A method as claimed in claim 1, wherein the light of different wavelengths is directed to the measuring window by means of a common optical conductor or different parts of the common optical conductor.

9. A measuring device for continuously measuring the Abbe number in a process liquid, the measuring device comprising:
means for generating light;
first directing means for directing the light through a measuring window in contact with the process liquid to the process liquid such that total reflection occurs on the contact surface of the measuring window and the process liquid;
second directing means for directing the part of the light that has been totally reflected to a sensor, whereby an image is formed on a light-sensitive surface of the sensor, the boundary between a light region and a dark region in the image corresponding to a critical angle at which the total reflection occurs; and
an arrangement for detecting the boundary between the light and the dark regions and for determining the dependency between the boundary of the light and the dark regions and the process liquid to be measured,
the means for generating light comprising means for successively generating light at wavelengths of substantially 486.1 nm, 589.3 nm and 656.3 nm,
the first directing means comprising optics being arranged to provide a suitable angular distribution for the tight,
the first directing means being arranged to direct the light of different wavelengths successively through the measuring window in contact with the process liquid to the process liquid,
the second directing means being arranged to direct the part of the light totally reflected at each wavelength successively to the sensor,
the arrangement for detecting the boundary between the light and the dark regions and for determining the dependency between the boundary of the light and the dark regions and the process liquid to be measured being arranged to perform the detection and determination at each wavelength, and
the measuring device further comprising a calculating unit for calculating the Abbe number by means of the refractive index values obtained from the aforementioned three wavelengths by using the formula known per se:

$$V_D = \frac{n_D - 1}{n_F - n_C}$$

where $n_D$ is the refractive index of the process liquid to be measured at a wavelength of 589.3 nm, $n_F$ is the refractive index at a wavelength of 486.1 nm, and $n_C$ is the refractive index at a wavelength of 656.3 nm.

10. A measuring device as claimed in claim 9, wherein the means for generating light at different wavelengths comprises three different light sources.

11. A measuring device as claimed in claim 10, wherein the light sources are arranged to emit light at the aforementioned wavelengths.

12. A measuring device as claimed in claim 10, wherein the light sources are light sources emitting white light and a filter is arranged in connection with each light source to provide a desired wavelength.

13. A measuring device as claimed in claim 9, wherein, at each wavelength, the dependency between the boundary of the light and the dark regions and the refractive index of the process liquid to be measured is arranged to be determined by utilizing information obtained from solutions with a known refractive index.

14. A measuring device as claimed in claim 9, wherein
the light of different wavelengths is arranged to be directed to the measuring window by using the first the directing means comprising lenses or mirrors or combinations thereof to provide a suitable angular distribution for the light and
the light that has been totally reflected is arranged to be directed to the light-sensitive surface of the sensor by using the second directing means comprising lenses or mirrors or combinations thereof.

15. A measuring device as claimed in claim 14, wherein the light-sensitive surface is arranged with respect to the second directing means at a distance that equals the focal length of the second directing means.

16. A measuring device as claimed in claim 9, wherein the first directing means directing light of different wavelengths to the measuring window comprises an optical conductor common to each wavelength or an optical conductor with different parts for different wavelengths.

17. A measuring device as claimed in claim 16, wherein the light of different wavelengths is arranged to be directed to the optical conductor by means of a diffusing member.

18. A measuring device as claimed in claim 17, wherein the diffusing member is ground glass.

19. A measuring device as claimed in claim 17, wherein the diffusing member is an integrating sphere, which is arranged to reflect light in a diffuse way multiple times until illumination is distributed equally on the surface of the sphere.

20. A measuring device as claimed in claim 9, wherein the means for generating light comprises light sources, and wherein, in addition to the calculating unit, the measuring device comprises a control unit, the control unit being arranged to receive a control signal from the calculating unit and to control the light sources, and the calculating unit being arranged to receive the information related to the images via the control unit, to calculate the refractive indices and the Abbe number derived therefrom, and to transmit a desired measurement signal to a desired location.

\* \* \* \* \*